US010357650B2

(12) United States Patent
Osypka

(10) Patent No.: US 10,357,650 B2
(45) Date of Patent: Jul. 23, 2019

(54) ELECTRODE TRANSITION SEAL FOR IMPLANTABLE LEAD BODY

(71) Applicant: Oscor Inc., Palm Harbor, FL (US)

(72) Inventor: Thomas P. Osypka, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 158 days.

(21) Appl. No.: 15/271,940

(22) Filed: Sep. 21, 2016

(65) Prior Publication Data

US 2017/0080215 A1    Mar. 23, 2017

Related U.S. Application Data

(60) Provisional application No. 62/221,212, filed on Sep. 21, 2015.

(51) Int. Cl.
*A61N 1/05*    (2006.01)

(52) U.S. Cl.
CPC .................. *A61N 1/0551* (2013.01)

(58) Field of Classification Search
CPC .................................................... A61N 1/0551
See application file for complete search history.

(56) References Cited

U.S. PATENT DOCUMENTS

| 5,433,742 | A | * | 7/1995 | Willis | A61N 1/056 607/116 |
| 5,580,699 | A | * | 12/1996 | Layman | A61N 1/05 216/65 |
| 2005/0021119 | A1 | * | 1/2005 | Sage | A61N 1/0529 607/122 |
| 2006/0116739 | A1 | * | 6/2006 | Betser | A61N 1/0556 607/48 |
| 2009/0264943 | A1 | * | 10/2009 | Barker | A61N 1/3752 607/2 |
| 2011/0054580 | A1 | * | 3/2011 | Desai | A61N 1/056 607/116 |

* cited by examiner

*Primary Examiner* — William J Levicky
(74) *Attorney, Agent, or Firm* — Locke Lord LLP; Scott D. Wofsy

(57) ABSTRACT

An implantable stimulation lead is disclosed that includes an elongated lead body having opposed proximal and distal end portions, the lead body being formed from a material having at least one circumferential seal region associated with the distal end portion thereof within which a cylindrical electrode is positioned, the seal region being formed from at least one transition component made from a material that is softer than the material from which the lead body is formed.

18 Claims, 3 Drawing Sheets

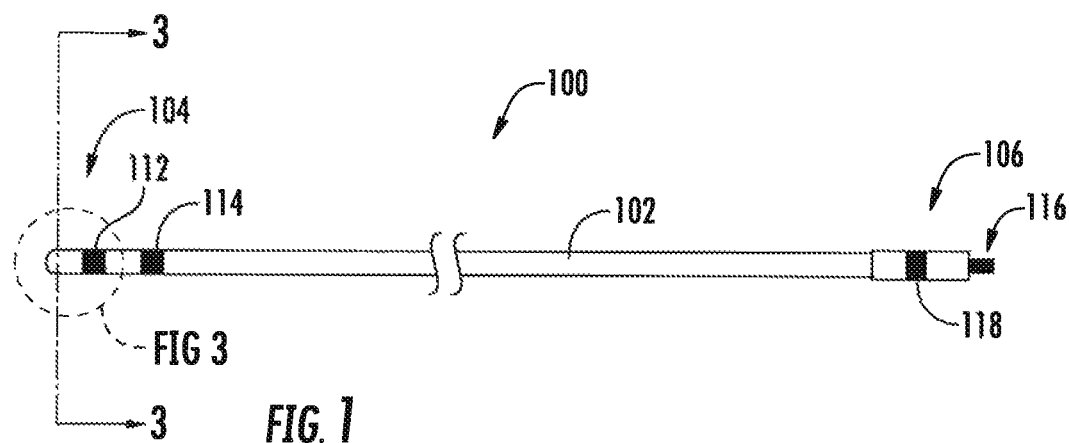
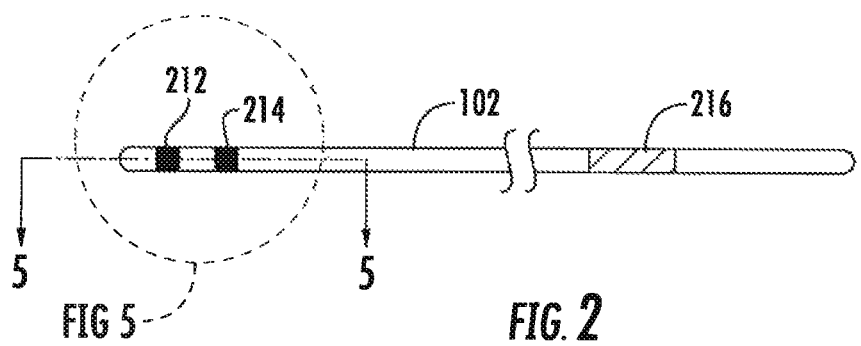

ELECTRODE TRANSITION SEAL FOR IMPLANTABLE LEAD BODY

CROSS-REFERENCE TO RELATED APPLICATION

The subject invention claims the benefit of and priority to U.S. Provisional Application Ser. No. 62/221,212 filed Sep. 21, 2015, the disclosure of which is herein incorporated by reference in its entirety.

BACKGROUND OF THE INVENTION

1. Field of the Invention

The subject invention is directed to a stimulation lead, and more particularly, to a low profile neuro stimulation lead having an elongated lead body with at least two electrically active electrodes positioned along a distal portion of the lead body.

2. Description of Related Art

Current implantable stimulation leads are typically designed with a lead body formed from a biocompatible polymeric material such as polyurethane, preferably having a durometer of about 55D or 90A on the Shore hardness scale. The use of polyurethane lead bodies is preferable, in particular with neuro stimulation leads, as compared to implantable grade silicone for several reasons.

First, polyurethane prevents the lead body from stretching during a tunneling implant procedure. Second, the lead body will have a smoother and more lubricious body surface, and third, they have a higher abrasion resistance when several leads are positioned next to each other and/or the lead has to be tunneled through small spaces such as the epidural.

Neuro stimulation leads commonly feature at least two stimulation electrodes, which are typically made from Platinum (Pt) and/or an alloy of Platinum and Iridium (Pt/Ir) or other electrically conductive biocompatible alloy materials, and they are typically connected through conductors to a stimulation source.

Current stimulation leads made with a polyurethane lead body have the advantages described above and can be normally sealed very well around the transition areas, for example, adjacent to the stimulation electrodes, to prevent fluid ingression. However, when these leads are bent in the area where the electrodes are positioned in an extreme way (e.g., more than 20 degrees), the transition areas between the polyurethane lead body and the stiff stimulation electrodes show areas of exposure. This could allow fluid and/or blood to enter between the electrodes and lead body into the interior of the lead body, possibly migrating to the electrically active connection areas. This could result in an electrical shortage, corrosion and possibly the malfunction of the stimulation system.

Therefore, a need exists in the art for a more compliant lead body construction that provides sealing characteristics in the transition areas between the compliant lead body and the stiff stimulation electrodes. The subject invention provides a solution.

BRIEF DESCRIPTION OF THE DRAWINGS

So that those skilled in the art to which the subject invention appertains will readily understand how to make and use the subject invention without undue experimentation, preferred embodiments thereof will be described in detail herein below with reference to certain figures, wherein:

FIG. 1 is a side elevational view of an elongated lead body having a pair of stimulation electrodes operatively associated with a distal end portion thereof and a connector operatively associated with a proximal end portion thereof;

FIG. 2 is a side elevational view of an elongated lead body having a pair of stimulation electrodes operatively associated with a distal end portion thereof and a stimulation source embedded into the proximal end portion thereof;

DETAILED DESCRIPTION OF PREFERRED EMBODIMENTS

Figure 3:
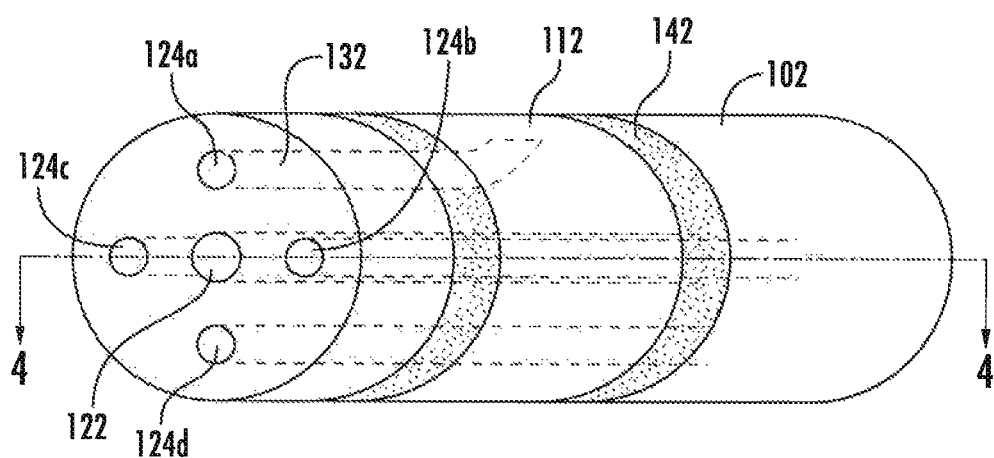
FIG. 3 is a detailed cross-sectional view of a sealed electrode transition region constructed in accordance with a preferred embodiment of the subject invention shown in FIG. 1.

Referring now to the drawings wherein like reference numerals identify similar structural features and/or elements of the subject matter disclosed herein, there is illustrated in FIG. 1 a stimulation lead in accordance with a preferred embodiment of the subject invention and designated generally by reference numeral 100.

The stimulation lead 100 includes an elongated lead body 102 having opposed proximal and distal end portions 104, 106. A pair of stimulation electrodes 112, 114 is operatively associated with the distal end portion 104 thereof. Each stimulation electrode 112, 114 is operatively associated with a stimulation source through a connector 116 positioned at the proximal end portion 106 of the lead body 102.

The stimulation source could be a neuro stimulator in form of a pulse generator (not shown), whereby the lead would be connected through a standardized connector to a header receptacle of the pulse generator and whereby silicone O-rings 118 on either the connector or generator receptacle side would provide a hemostatic seal to prevent fluid ingression. A stimulation lead 100 having a connector 116 of this type is illustrated in FIG. 1. Alternatively, the stimulation source could be an electrically active circuit 216 with a conductive charging coil inside the lead body 202 operatively associated with electrodes 212, 214, as shown for example with simulation lead 200 in FIG. 2. In either configuration, it is desirable for the stimulation lead to be completely sealed from fluid ingression, so as to prevent electrical shortage and the potential for long term corrosion.

The lead body 102 may be a single lumen channel or may include a plurality of circumferentially spaced lumens 124a-d surrounding an interior lumen 122, as seen best in FIG. 3. The interior lumen 122 may be for placement of a stylet or guidewire while remaining lumens 124a-d may be used for conductors, including conductor 132 connecting electrode 112 to simulation source.

Figure 4:
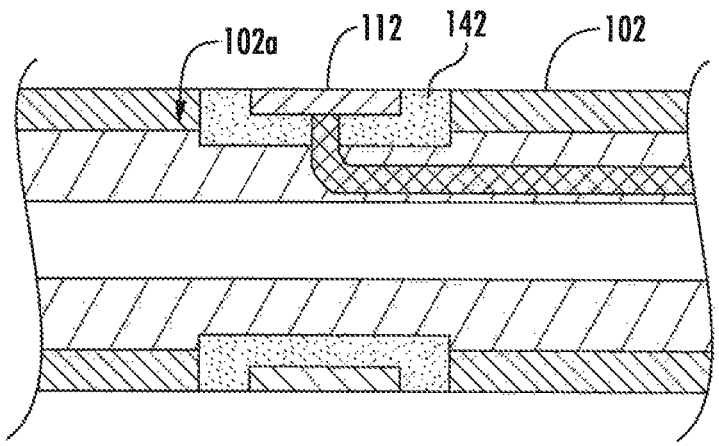
FIG. 4 is a cross-sectional view taken along line 4-4 of FIG. 3, showing the sealed electrode transition region of the subject invention.

Referring to FIGS. 3 and 4, each electrode 112, 114 along the distal portion 104 of the lead body 102 is positioned within a transition component 142 defining a seal region for neuro stimulation. The electrodes 112, 114 are preferably configured at least as a bipolar stimulation assembly and include at least two spaced apart cylindrical ring electrodes. It is envisioned however, that the electrode assembly could be configured as a multi-polar assembly with between four (4) and sixteen (16) or more spaced apart electrodes. The electrodes are formed from Platinum (Pt) and/or an alloy of Platinum and Iridium (Pt/Ir) or other electrically conductive biocompatible alloy materials.

It is envisioned that the electrodes can be positioned either on top of the elongated lead body or the lead body wall can be reduced in diameter (for example by means of centerless grinding or laser ablation) in the area of the electrode location to allow a seamless atraumatic smooth transition between the electrodes and the lead body, as shown in FIGS. 3 and 4.

The transition component 142 of the seal region is made from a material that is relatively softer than the material from which the lead body 102 is formed. Accordingly, when the lead body 102 is bent in this region, the softer transition components 142 will advantageously comply more readily than the harder lead body 102, so as to maintain a fluid seal in relation to the electrode 112, so that the interior 102a of the lead body adjacent to the electrode will not become exposed. This will prevent the ingress of fluid or blood into the interior lumen 122 of the lead body 102, and thereby eliminate the possibility of an electrical short or corrosion of the internal conductors located within the lead body 102.

Preferably, the lead body 102 is formed from a biocompatible polymeric material and the transition components 142 are formed from a biocompatible polymeric material. More preferably, the lead body 102 is formed from a polyurethane material and the transition components are formed from a silicone material. In particular, the lead body 102 is formed from a biocompatible polymeric material having a relatively hard durometer and the transition components are formed from a biocompatible polymeric material having a durometer of relatively medium hardness. More particularly, the lead body is formed from a material having a Shore A hardness of about 90 (55D), and the transition components are formed from a material having a Shore A hardness of about 70 or softer.

Figure 5:
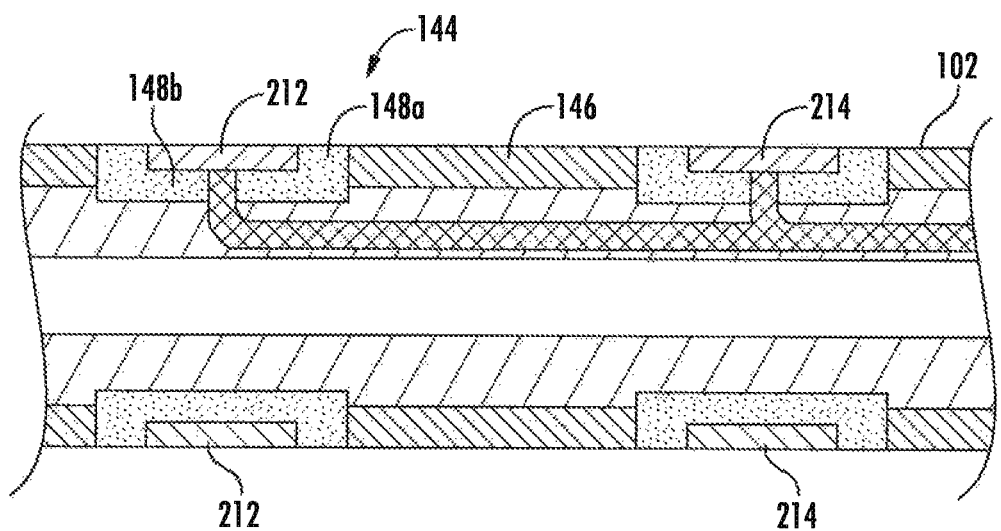
FIG. 5 is a detailed cross-sectional view taken along line 5-5 of FIG. 2, showing a distal end portion of the implantable stimulation lead of the subject invention, illustrating the structural components of the sealed transition region associated with the electrode assembly.

As best seen in FIG. 5, the circumferential seal region includes a pair of axially spaced apart transition components 144 that are each defined by a cylindrical sealing plug 148. Each cylindrical electrode 212, 214 surrounds at least portions of the axially spaced apart transition components 144 associated therewith. More particularly, the seal plugs 148 each have an enlarged diameter portion 148a that interacts with the lead body and a reduced diameter portion 148b that interacts with the cylindrical electrode 212, 214. A cylindrical body spacer 146 is disposed between two adjacent electrodes 212, 214.

While the subject invention has been shown and described with reference to preferred embodiments, those skilled in the art will readily appreciate that various changes and/or modifications may be made thereto without departing from the spirit and scope of the subject invention as defined by the appended claims.

What is claimed is:

1. An implantable stimulation lead comprising:
an elongated lead body having opposed proximal and distal end portions, the lead body formed from a first material, and having at least one circumferential seal region associated with the distal end portion thereof within which a cylindrical electrode is positioned, the seal region being formed from at least one transition component made from a second material that is softer than the first material from which the lead body is formed, wherein the transition component includes a reduced diameter portion that interacts with the cylindrical electrode and is bounded by enlarged diameter portions that interact with the lead body.

2. An implantable stimulation lead as recited in claim 1, wherein the distal end portion of the lead body includes a pair of axially spaced apart transition components.

3. An implantable stimulation lead as recited in claim 2, wherein a cylindrical body spacer is disposed between the pair of axially spaced apart transition components.

4. An implantable stimulation lead as recited in claim 1, wherein the lead body is formed from a biocompatible polymeric material.

5. An implantable stimulation lead as recited in claim 1, wherein the at least one transition component is formed from a biocompatible polymeric material.

6. An implantable stimulation lead as recited in claim 1, wherein the lead body is formed from a polyurethane material.

7. An implantable stimulation lead as recited in claim 1, wherein the at least one transition component is formed from a silicone material.

8. An implantable stimulation lead as recited in claim 1, wherein the lead body is formed from a material having a Shore A hardness of about 90.

9. An implantable stimulation lead as recited in claim 1, wherein the at least one transition component is formed from a material having a Shore A hardness of about 70 or softer.

10. An implantable stimulation lead as recited in claim 1, wherein the lead body is formed from a biocompatible polymeric material having a relatively hard durometer.

11. An implantable stimulation lead as recited in claim 1, wherein the lead body is formed from a biocompatible polymeric material having a durometer of relatively medium hardness.

12. An implantable stimulation lead as recited in claim 1, wherein the cylindrical electrode is formed from Platinum.

13. An implantable stimulation lead as recited in claim 1, wherein the cylindrical electrode is formed from a Platinum and Iridium alloy.

14. An implantable stimulation lead comprising:
an elongated cylindrical lead body having opposed proximal and distal end portions, and being formed from a first biocompatible polymeric material having a Shore A hardness of about 90, the distal end portion of the lead body including at least one cylindrical transition component that is made from a second biocompatible material having a Shore A hardness of about 70 or softer, wherein the at least one cylindrical transition component has a reduced diameter portion that accommodates a cylindrical electrode and is bounded by enlarged diameter portions that interact with the lead body to provide a smooth transition between the electrode and the lead body.

15. An implantable stimulation lead as recited in claim 14, wherein the lead body is formed from a polyurethane material.

16. An implantable stimulation lead as recited in claim 14, wherein the transition component is formed from a silicone material.

17. An implantable stimulation lead as recited in claim 14, wherein the electrode is formed from Platinum.

18. An implantable stimulation lead as recited in claim 14, wherein the electrode is formed from a Platinum and Iridium alloy.

* * * * *